(12) United States Patent
Shelyakov et al.

(10) Patent No.: US 7,674,225 B2
(45) Date of Patent: Mar. 9, 2010

(54) ANATOMIC DEVICE

(75) Inventors: Alexander Vasilievich Shelyakov, Moscow (RU); Vladimir Vitoldovich Sokolvskiy, Moscow (RU); Alexander Alexandrovich Korneev, Moscow (RU)

(73) Assignee: International Innovative Solutions, LLC, Falmouth, MA (US)

( * ) Notice: Subject to any disclaimer, the term of this patent is extended or adjusted under 35 U.S.C. 154(b) by 75 days.

(21) Appl. No.: 11/456,184

(22) Filed: Jul. 7, 2006

(65) Prior Publication Data

US 2006/0241341 A1    Oct. 26, 2006

Related U.S. Application Data

(63) Continuation of application No. PCT/RU2004/000116, filed on Mar. 26, 2004.

(51) Int. Cl.
*A61F 5/00* (2006.01)

(52) U.S. Cl. ............................................... 600/41

(58) Field of Classification Search ............ 600/37–41; 128/883
See application file for complete search history.

(56) References Cited

U.S. PATENT DOCUMENTS

| | | | |
|---|---|---|---|
| 4,203,432 A * | 5/1980 | Koch ........................... | 600/41 |
| 4,498,466 A | 2/1985 | Pomeranz | |
| 4,723,538 A | 2/1988 | Stewart et al. | |
| 4,953,542 A | 9/1990 | Tsirjulnikov et al. | |
| 5,027,800 A | 7/1991 | Rowland | |
| 5,377,692 A | 1/1995 | Pfeil | |
| 5,800,340 A | 9/1998 | Gekhter et al. | |
| 6,221,447 B1 | 4/2001 | Munn et al. | |
| 6,273,888 B1 * | 8/2001 | Justis ........................ | 606/272 |
| 6,306,080 B1 | 10/2001 | Mitchell et al. | |
| 6,390,095 B1 | 5/2002 | Magnusson | |
| 6,478,656 B1 | 11/2002 | Khouri | |
| 6,485,408 B2 | 11/2002 | Orten | |
| 6,547,717 B1 | 4/2003 | Green | |
| 2002/0022760 A1 | 2/2002 | Orten | |
| 2003/0024536 A1 | 2/2003 | Bagby | |

(Continued)

FOREIGN PATENT DOCUMENTS

EP    1210921 A2    6/2001

(Continued)

*Primary Examiner*—John P Lacyk
(74) *Attorney, Agent, or Firm*—Houston Eliseeva LLP

(57) ABSTRACT

An anatomical device comprising an unclosed curvilinear frame with distal ends, forming an aperture for receiving a penis. The unclosed curvilinear frame is made of a material with shape memory effect, thus forming a compressing element set to memorize the shape of the curvilinear figure repeating the external contour of a penis base in erected state. The area of the setting shape is by 30-50% less than that of the cross-section of penis base at maximum erection. An anatomical device built as a closed curvilinear frame, containing an unclosed curvilinear frame with connected distal ends, forming an aperture for receiving a penis. The unclosed curvilinear frame is made of a material with shape memory effect, thus forming a compressing element that is set to memorize the shape of the curvilinear figure repeating the external contour of a penis base in erected state. The area of the setting shape is by 30-50% less than that of the cross-section of penis base at maximum erection. In active working state, the closed curvilinear frame forms a loop behind the distal ends, for releasing a urethra.

18 Claims, 6 Drawing Sheets

U.S. PATENT DOCUMENTS

2004/0020494 A1     2/2004    Burpee
2005/0020871 A1     1/2005    Tozzi et al.

FOREIGN PATENT DOCUMENTS

| | | |
|---|---|---|
| JP | 4170950 | 6/1992 |
| JP | 6047069 | 2/1994 |
| JP | 07231905 | 9/1995 |
| JP | 2002085437 | 3/2002 |
| JP | 2002085438 | 3/2002 |
| RU | 2115391 C1 | 7/1998 |
| SU | 1688865 A1 | 11/1991 |
| WO | WO98/22036 A1 | 5/1998 |
| WO | WO2004/010906 A1 | 2/2004 |

* cited by examiner a  b

ANATOMIC DEVICE

RELATED APPLICATIONS

This application is a Continuation of PCT application serial number PCT/RU2004/000116 filed on Mar. 26, 2004 which is incorporated herein by reference in its entirety.

FIELD OF THE INVENTION

The invention relates to the area of medicine, specifically to sexual pathology, and in particular to the devices providing enhancement of sexual pleasure during intercourse.

BACKGROUND OF THE INVENTION

There is a known anatomic, disposable, compressing device (U.S. Pat. No. 6,306,080, published Oct. 23, 2001, A61F5/00) for the penis which contains a strip of flexible and elastic material in the form of a closed curvilinear figure. This figure is placed in such a manner that the internal surface of the flexible material is located around the penis, forming an aperture. A fastener is used to secure the device around the penis.

There is also known an anatomic device (U.S. Pat. No. 2,115,391, published Jul. 20, 1998, A61F5/41) which represents an orgiastic collar with some elements of sex-correction. This device contains an undulating surface of variable height on its outer side. It also contains a segment with undulating outside and inside faces, thus on an inside face of a segment the undulating surface also has variable height. The orgiastic collar also contains an elastic collar which allows self-regulation for the user.

However, the aforementioned devices lack the ability for self-regulation of the compression by the user while in the act of using the device: adjustment of compression by the user can only be done before the intercourse. Because the stress of the compression can not be changed while the device is in use, injury can result at end of the sexual act or after loss of erection if they're not removed in a timely manner. In addition, constriction of the urethra by said devices makes difficulties for outflow of sperm and prostate gland secretions, resulting in serious physiological impairments over the long-term. Also, the putting on, as well as removal, of the devices does not provide for com-fort and convenience for the user.

Impotence treatment anatomical device (U.S. Pat. No. 1,688,865 of Dec. 30, 1991, A61F5/41) made of wire, containing penis head clamp, penis base clamp, and the intermediate steering clamp, all of those combined by connecting rods. This is a closed-contour device made of the material with two-way shape memory effect that allows for memorizing two states of shape, "hot" and "cold" ones; connecting rods are located in the bottom and top parts of the device. For "hot" condition, the steering clamp is shaped as two closed half-arcs, the base and head penis clamps are shaped as non-closed rings, the connecting rods are closed. For "cold" state, clamps at the head and the base of a penis have horseshoe-shaped form, the steering clamp has an arc-shaped form, and the connecting rods are opened.

The key drawback of this device is the inconveniency patients experience while putting on and removing the device. Besides, since its design does not include use of compressing force at the penis base clamp, effective stimulation and erection maintenance are not achieved.

There exists a patented erection ring device (U.S. Pat. No. 6,390,095 of May 21, 2002, A61F5/41), providing continuous compression in a penis. The ring is made of medical silicon rubber, it provides compressing force equal to 1.5 kg (±0.5 kg) also is capable to change its diameter by over 150%. The ring consists of several parts with different rigidity and/or cross-section, and the part located in the urethral zone has lower rigidity than other parts.

The shortfall of this device is, again, lack of comfort putting it on or off, and continuous compression in a penis can lead to injury if the device is not removed promptly following the sexual intercourse or loss of erection.

Of special interest in the area is the anatomical device (U.S. Pat. No. 2003024536 of Feb. 6, 2003, A61F5/41) built on the basis of a flexible unclosed curvilinear frame. It consists of a top part and two legs, left and right, with distal ends, that form aperture for receiving the penis. The size of the aperture is adjusted by positioning top, left and right leg. For fixation of the device in its closed position, the distal ends are connected by a loop from a rigid material, allowing space for releasing urethra.

This device is the closest prototype to the solution we propose for patenting.

Main drawback of this device is its complex design, resulting in inconvenient manipulations while putting the device in place or removing it, difficult adjustment of compression force (that cannot be changed in working state, thus leading to potential injury should the device not be removed promptly after the intercourse or loss of erection).

SUMMARY OF THE INVENTION

The principle advancements of the claimed invention are the increase in safety and efficiency of the device by maintaining continuous compression of a penis during prolonged sexual intercourse; decreasing rigidity of the device following the intercourse or loss of erection, increase of comfort while putting on or taking off this anatomical device, general design simplification.

This task is addressed by making an anatomical device consisting of an unclosed curvilinear frame with distal ends, forming an aperture for receiving a penis. The unclosed curvilinear frame is made of a material with shape memory effect (SME), thus forming a compressing element which is set to memorize the shape of the curvilinear figure repeating the external contour of a penis base in erected state. The area of the setting shape is by 30-50% less than that of the cross-section of penis base at maximum erection.

The compressing element is made of SME material that allows for 5 to 10 times increase in compressing element rigidity while in the active working state, as compared to its initial condition.

The unclosed curvilinear frame is covered by easily deformable or flexible material.

The distal ends are connected by easily deformable or flexible material, thus forming the closed curvilinear frame.

The unclosed curvilinear frame is covered by easily deformable or flexible material, forming the closed curvilinear frame.

In its working state, the closed curvilinear frame forms a loop of easily deformable or flexible material behind the distal ends for releasing a urethra.

The easily deformable or flexible material is made of silicone or elastomer, alternatively latex or leather or metal.

Also, this task is addressed by designing an anatomical device as a closed curvilinear frame, containing an unclosed curvilinear frame with connected distal ends, forming an aperture for receiving a penis. The unclosed curvilinear frame is made of a material with shape memory effect (SME), thus forming a compressing element that is set to memorize the shape of the curvilinear figure repeating the external contour of a penis base in erected state. The area of the setting shape is by 30-50% less than that of the cross-section of penis base at maximum erection. In active working state, the closed curvilinear frame forms a loop behind the distal ends, for releasing a urethra.

The compressing element is made of SME material that allows for 5 to 10 times increase in compressing element rigidity while in the active working state, as compared to its initial condition.

The distal ends are connected by easily deformable or flexible material, thus forming the closed curvilinear frame.

The unclosed curvilinear frame is covered by easily deformable or flexible material, forming the closed curvilinear frame.

The easily deformable or flexible material is made of silicone or elastomer, alternatively latex or leather or metal.

Also, the task in question is addressed by designing an anatomical device as a closed curvilinear frame, which contains an unclosed curvilinear frame with connected distal ends forming two parts with different rigidities and also an aperture for receiving a penis. With this design, a greater part of the closed curvilinear frame is made of a material with shape memory effect (SME): this part forms the compressing element of greater rigidity if compared to the other part which in its turn is made of easily deformable or flexible material, which in working state forms a loop behind the distal ends, for releasing the urethra.

The compressing element is set to memorize the shape of the curvilinear figure repeating the external contour of a penis base in erected state. The area of the setting shape is by 30-50% less than that of the cross-section of penis base at maximum erection.

The compressing element is made of SME material that allows for 5 to 10 times increase in compressing element rigidity while in the active working state, as compared to its initial condition.

The easily deformable or flexible material is made of silicone or elastomer, alternatively latex or leather or metal.

BRIEF DESCRIPTION OF THE DRAWINGS

In the accompanying drawings, reference characters refer to the same parts throughout the different views. The drawings are not necessarily to scale; emphasis has instead been placed upon illustrating the principles of the invention. Of the drawings.

The declared invention is illustrated by specific implementation examples and by the following drawings.

DETAILED DESCRIPTION OF THE PREFERRED EMBODIMENTS

Figure 1:
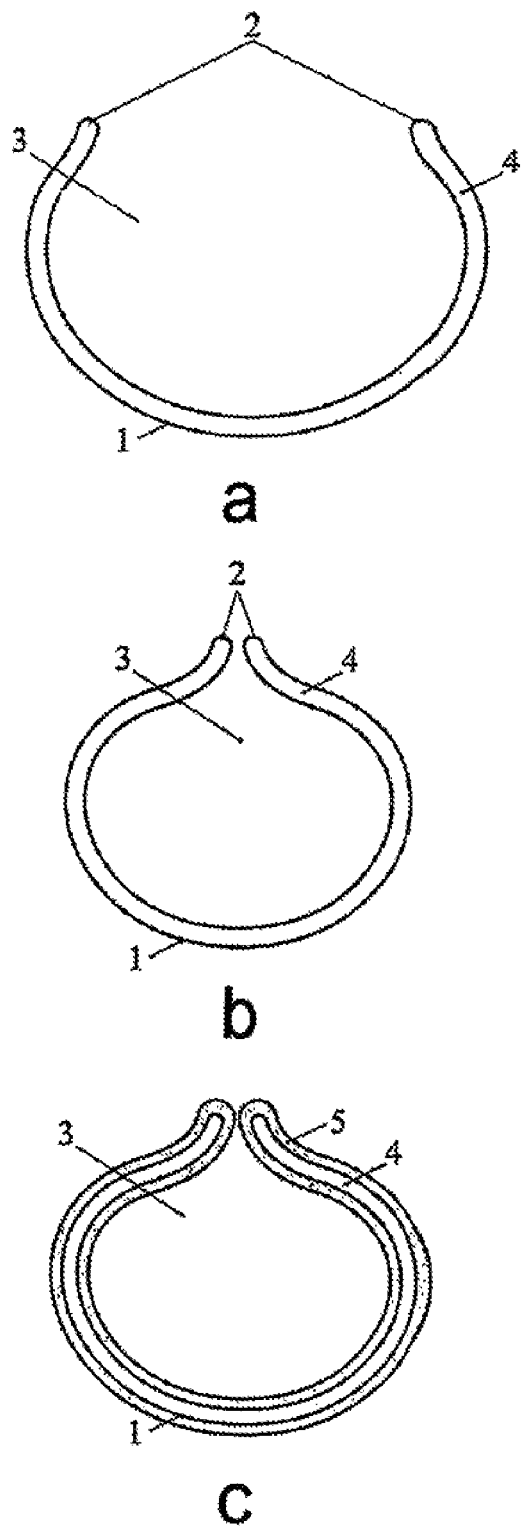
FIG. 1 is a graphic presentation showing the anatomical device designed according to the first mentioned variant.

The anatomical device presented in FIG. 1 contains the unclosed curvilinear frame (1) with distal ends (2), forming an aperture (3) for receiving a penis. The unclosed curvilinear frame (1) is made of a material with shape memory effect, forming compressing element (4).

Compressing element (4) is set to memorize the shape of the curvilinear figure repeating the external contour of a penis base in erected state. The area of the setting shape is by 30-50% less than that of the cross-section of penis base at maximum erection.

The compressing element is made of SME material that allows for 5 to 10 times increase in compressing element rigidity while in the active working state (FIG. 1b), as compared to its initial condition (FIG. 1a).

The unclosed curvilinear frame is covered by easily deformable or flexible material (5), FIG. 1c.

Figure 2:
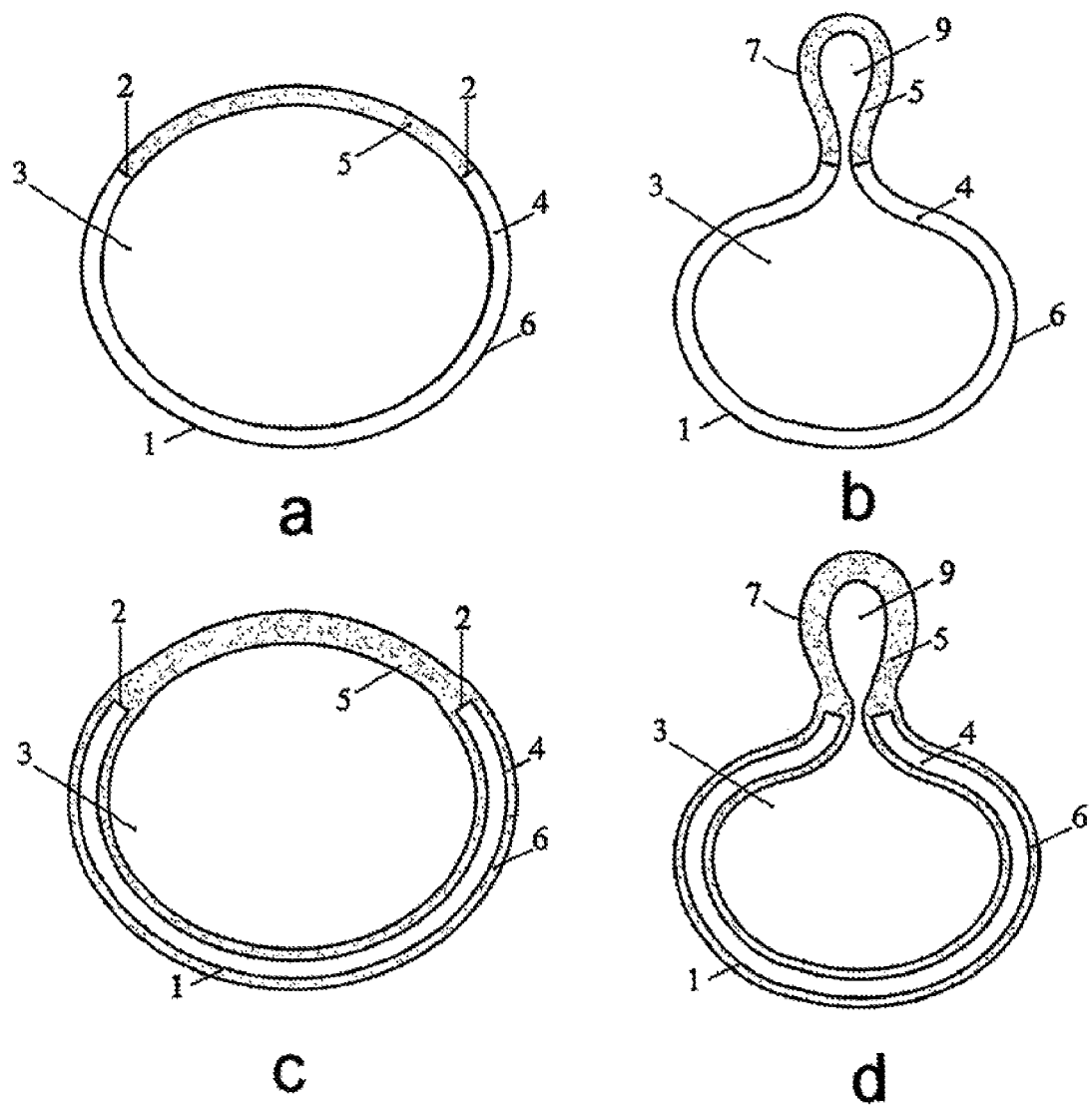
FIG. 2 illustrates the second possible design of the device.

The distal ends (2) are connected by easily deformable or flexible material (5), thus forming the closed curvilinear frame (6) (FIG. 2 a,b).

The unclosed curvilinear frame (1) is covered by easily deformable or flexible material (5) (FIG. 2 c,d), forming the closed curvilinear frame (6).

In its working state (FIG. 2 b,d), the closed curvilinear frame (6) forms a loop (7) of easily deformable or flexible material behind the distal ends for releasing a urethra.

The easily deformable or flexible material (5) is made of silicone or elastomer, alternatively latex or leather or metal.

The anatomical device in FIG. 2 is designed as a closed curvilinear frame (6), containing an unclosed curvilinear frame (1) with connected distal ends (2), forming an aperture (3) for receiving a penis and a loop (7) behind the distal ends (2), for releasing urethra; the unclosed curvilinear frame is made of a material with shape memory effect (SME), thus forming a compressing element (4) that is set to memorize the shape of the curvilinear figure repeating the external contour of a penis base in erected state. The area of the setting shape is by 30-50% less than that of the cross-section of penis base at maximum erection.

The compressing element (4) is made of SME material that allows for 5 to 10 times increase in compressing element rigidity while in the active working state (FIG. 2b), as compared to its initial condition (FIG. 2a).

The distal ends (2) are connected by easily deformable or flexible material (5), thus forming the closed curvilinear frame (6).

The unclosed curvilinear frame 1 is covered by easily deformable or flexible material (5), forming the closed curvilinear frame (6) (FIGS. 2c,d).

The easily deformable or flexible material (5) is made of silicone or elastomer, alternatively latex or leather or metal.

Figure 3:
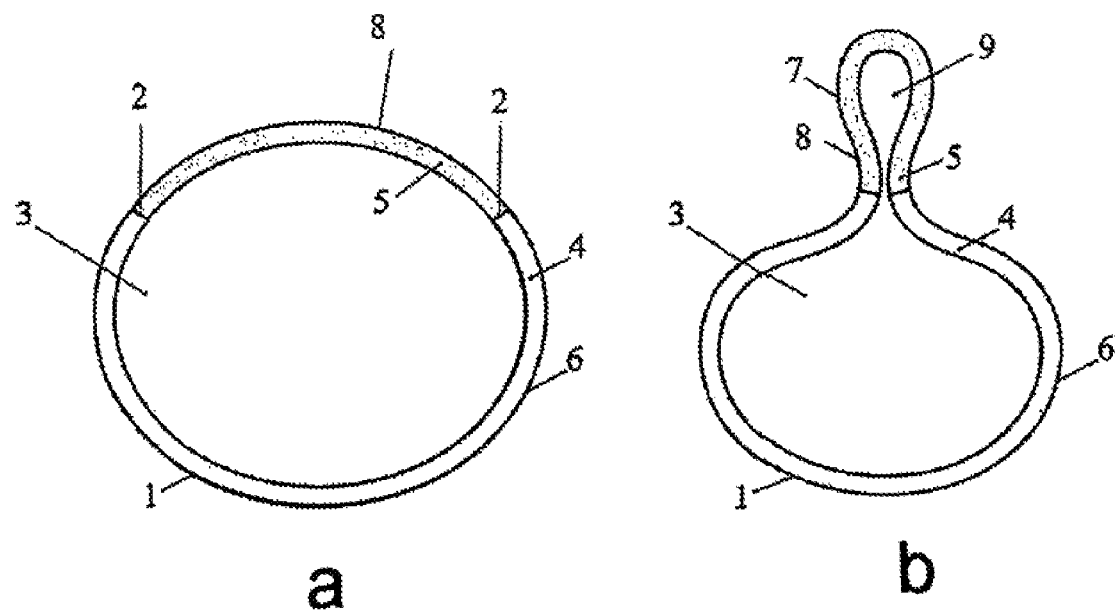
FIG. 3 shows the third possible device design.

The anatomical device in FIG. 3 is designed as a closed curvilinear frame (6), which contains an unclosed curvilinear frame (1) with connected distal ends (2) forming two parts (4 and 8) with different rigidities and also an aperture (3) for receiving a penis. With this design, the greater and the more rigid part (4) of the closed curvilinear frame is made of a material with shape memory effect (SME): this part forms the compressing element (4); the other part (8) is located behind the distal ends (2); it is less rigid, made of easily deformable or flexible material (5), and in working state it forms a loop (7) for releasing the urethra.

The compressing element (4) is set to memorize the shape of the curvilinear figure (1) repeating the external contour of a penis base in the erected state. The area of the setting frame is by 30-50% less than that of the cross-section of penis base at maximum erection.

The compressing element (4) is made of SME material that allows for 5 to 10 times increase in compressing element (4) rigidity while in the active working state, as compared to its initial condition.

The easily deformable or flexible material (5) is made of silicone or elastomer, alternatively latex or leather or metal.

For all the anatomical devices shown in FIGS. 1, 2, 3, the unclosed curvilinear frame (1) is made of material demonstrating shape memory effect (further referred to as SME), for example, a titanium nickelide (TiNi)—based alloy. The composition of the chosen SME material is selected so that the compressing element (4), once exposed to heat beyond 36° C., increases its rigidity by 5-10 times against its regular rigidity at temperatures below 25° C. The compressing element (4) is set to memorize the shape of the curvilinear figure repeating an external contour of a penis base in the erected state, but area of the setting frame is by 30-50% smaller that the area of penis base cross-section at maximum erection. Thermo-mechanical processing of the compressing element (4) can be performed, for example, in a muffle furnace at temperatures within 450-550° C. range, for 10-60 minutes, while monitoring the properties of the chosen SME material.

Figure 5:
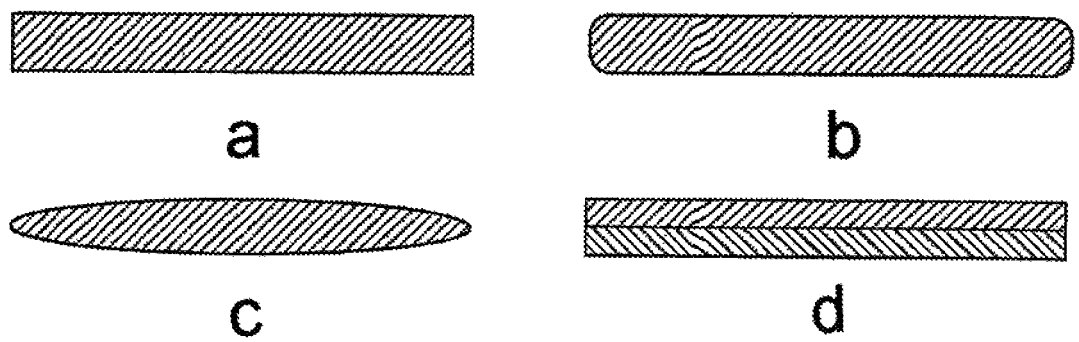
FIG. 5 shows the cross-section of a compressing element made of single or multiple plates of material with shape memory effect.
Figure 6:
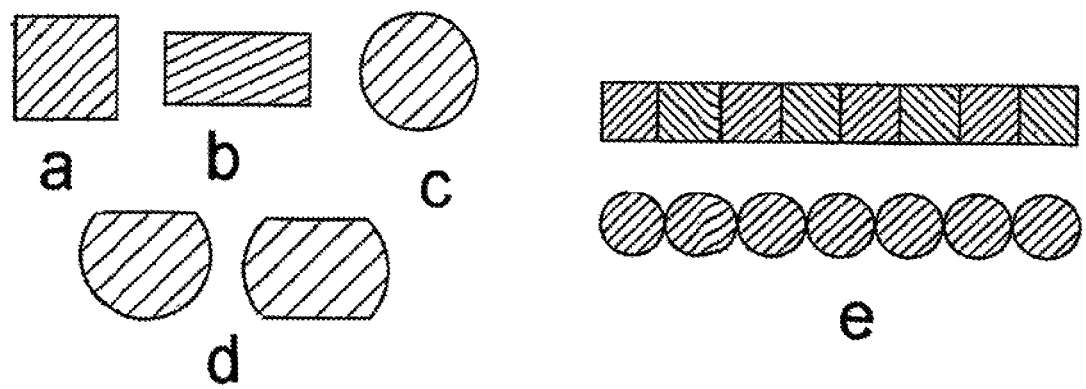
FIG. 6 shows the cross-section of a compressing element made of single or multiple pieces of shape memory wire.

The geometrical parameters of the SME compressing element (4), specifically its cross-section and length, are set to provide the compression of $(1.0-1.5) \times 10^4$ Pa at T>36° C. (depending on the individual parameters of a penis), sufficient to limit blood flow out of the penis in both languid and erected state. The SME compressing element (4) can be made, for example, of TiNi or TiNiCu alloys, in the following formats:

plates with rectangular cross-section (FIG. 5a), e.g. 0.8 mm by 10 mm, rectangular cross-section with rounded edges (FIG. 5b) or oval cross-section (FIG. 5c);

spring comprised of two or more plates (FIG. 5d);

single piece of wire with square (FIG. 6a), rectangular (FIG. 6b), round (FIG. 6c) or round, flattened with one or from two sides, (FIG. 6d), cross-section;

several connected (for instance, welded) pieces of wire (FIG. 6e).

The length of the compressing element (4) can be set to different values according to length of a penis base contour in the excited state, for instance, to cover the range of dimensions: 70 mm, 80 mm, 90 mm, 100 mm, 110 mm. These allow to adapt and to use the device for a penis of any male patient.

Connection of the easily deformable or flexible material (5) with the compression element (4) distal ends (2) is performed by standard procedures: for instance, connection of an SME plate or an SME wire to a silicone tube is implemented by thermal contraction (shrinking).

Functioning of the proposed anatomical device.

Figure 4:
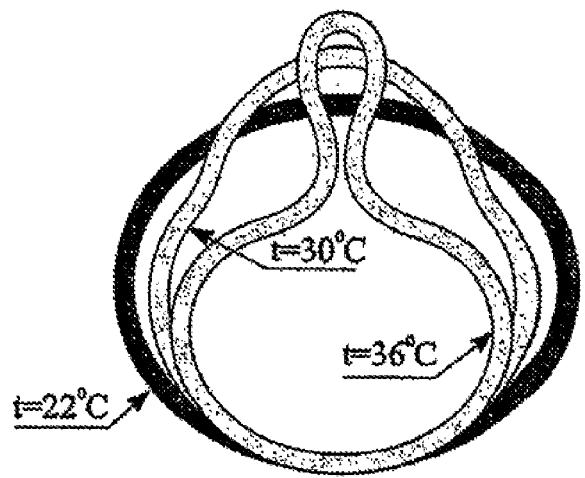
FIG. 4 illustrates how the anatomical device changes its shape with temperature change.
Figure 7:
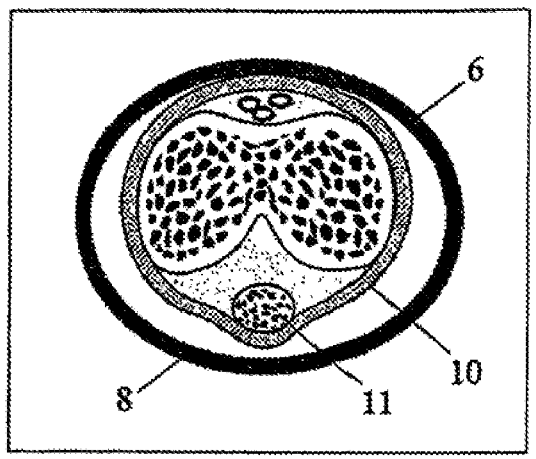
FIG. 7a-c illustrates the anatomical device when put on the penis base: (a)—in initial condition, (b)—in working state.
Figure 7:
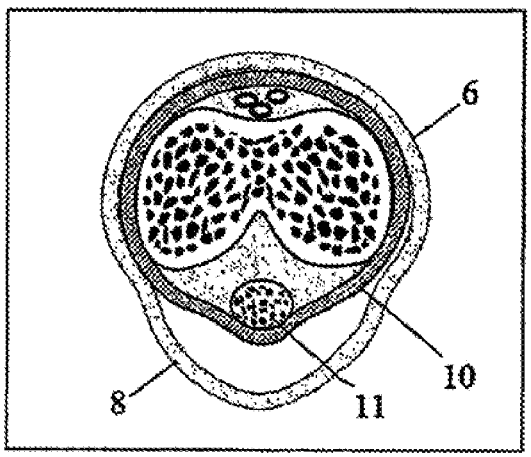
Figure 7:
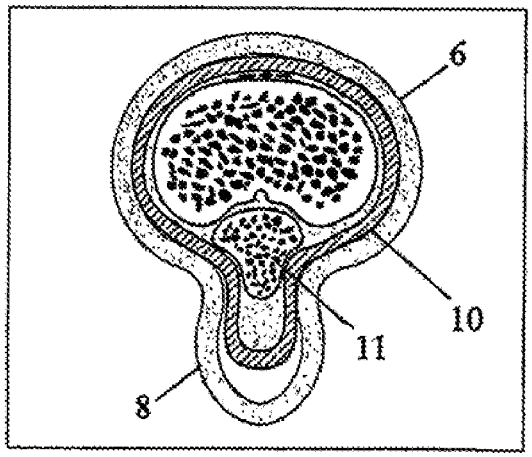

In initial condition, at temperatures below 25° C., the anatomical device is a plastic bracelet (collar) of unclosed curvilinear shape (1) or the closed curvilinear shape (6), for instance, resembling a ring or an ellipse (FIGS. 1a, 2a,c, 3a), with the minimal diameter exceeding the maximum penis cross-section size in both languid and excited states. As a result, unlike the existing analogies and the prototype, the proposed device can be safely and effortlessly placed at the penis base in any condition (at any stage of erection), thus not just providing comfort of putting on the device but also minimizing potential injuries to a penis (10) (FIG. 7). The easily deformable or flexible parts (5, 8) of the device are placed opposite to the urethra (11). When exposed to the heat of the human body (penis), the SME material of the compressing element (4) starts undergoing phase (reverse martensitic) transformation, as a result of which the element 4 begins to recover the shape it was set to memorize, switching to active working condition (FIG. 4) and gradually covering the penis 10 (FIG. 7b). Simultaneously with temperature increase, rigidity of the SME compressing element (4) grows and its compressing force increases. As the internal sizes of the setting shape of the SME compressing element (FIGS. 1b,c, 2b,d, 3b) are less than external sizes of the penis base, the compressing element 4 starts progressively (but comfortably) compressing the penis (10)(FIG. 7), restricting reverse blood outflow from the penis and, thus leading to arising and/or enhancing erection. The maximum stress of compression and, consequently, maximum erection during the sexual intercourse is achieved when the temperature of the device reaches the maximum values (above 36° C.). This is based on the fact that body temperature increases along with the increase of excitation, and also because when the female genitals cover the device during the intercourse, they provides additional source of heat as well as prevent heat transfer away from the device.

The important circumstance is that the urethra area is squeezed out through the unclosed part of the SME compressing element (4) into space free from element (4) (FIGS. 1b,c), or into space 9 (FIGS. 2b,d, 3b) which is limited by soft elastic parts (5, 8) of the device (forming loop (7) for releasing the urethra (11) (FIG. 7c)). Therefore, harmful compressing effect on the urethra is ruled out.

In contrast to the analogues and the prototype, compressing effect of which is based on elastic properties of working elements, the proposed anatomical device provides constant penis compression at temperatures above 36° C. due to non-linear relation of stress and deformation for SME materials. Specifically, the continuous constant penis compression is maintained during the initial occurrence of erection from languid state, as well as during the sexual intercourse—even if at a certain phase of a prolonged sexual act the elasticity (pressure of blood) and cross-section of a penis change. Should the former occur, the device sizes can change elastically, adapting for parameters of penis and current degree of its excitation and providing the compression necessary for maintaining erection even at partial excitation decrease (for example, when preventing premature ejaculation).

After the completion of a sexual intercourse resulting in ejaculation (or voluntary refusal to continue a sexual act), there occurs softening of a penis, and also the decrease in temperature of the SME compressing element (4) because of dropping penis temperature and increased heat transfer away from the compressing element, resulting in essential (by several times) reduction in compression force in element (4). Thus, the erection diminishes avalanche-like, and the device virtually falls off itself. As compared to the prototype, this allows for easier and safer removal of the anatomical device from a penis. If necessary, the device can be easily unclenched to its initial condition (FIGS. 1a, 2a,c, 3a, 7a) prior to removal. Besides, the above mentioned properties of the proposed anatomical device allow to avoid serious injuries, stemming from stagnant blood in a penis which occurs if for some reason any other device stays on penis base for too long (a few hours or more, as a result of falling asleep, for example).

Completely independent reversal of the anatomical device to its initial opened condition (shown on FIGS. 1a, 2a,c, 3a, 7a) when cooled down without any use of additional deformation of the device by hands can be provided by the following means:

precise selection of proper rigidity for soft parts (5, 8) of the device;

covering the compressing element (4) with elastic casing, for example, silicone (FIGS. 1c, 3c);

introduction of an additional elastic element: for example, an elastic metal plate coupled to the SME alloy plate with a spring.

Since SME alloys possess the characteristic of transformation plasticity, consisting in abnormal decrease in material rigidity when cooled down to the temperature point at which the direct martensitic transformation started, the presence of even minor reverse elastic force (in some cases just a fraction of SME compression element (4) rigidity at 25° C.) causes deformation of a compressing element 4 during cooling from its heated condition, thus returning the device to its initial opened position.

Figure 8:
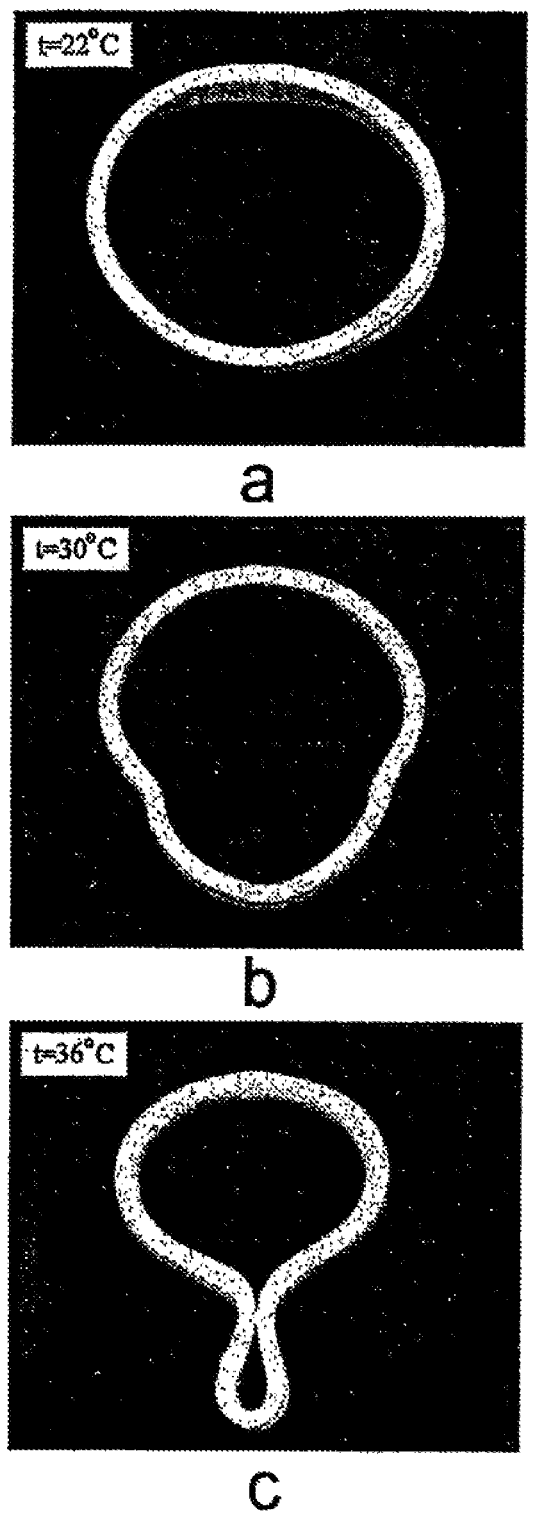
FIG. 8a-c contains photographs showing device implementation examples.

FIG. 8 shows photos of a practical implementation of the proposed anatomical device that has been built and tested. The device was made of a plate from TiNi alloy, covered by a medical silicone tube.

Summarizing all the claims, the proposed anatomical device has the following advantages as compared to its analogues:

Constant penis compression at T>36° C. with adjustment of the device compressing element sizes depending on parameters and an excitation degree of a penis.

Smooth increase in compression force of the SME element when heated by body warmth, reaching the maximum during a sexual intercourse.

Reduction of compression force of the SME element when cooled down after the end of an intercourse.

Improved easiness and comfort of putting the device in place (onto the penis base) and its removal, allowing to avoid injuries to a penis.

Ruling out any harmful influence on a urethra.

Simplicity of the device design.

All of the above sum up in increased safety comfort and efficiency in using the device, as well as essential simplification of the device compared to its prototype.

Possible Applications

The proposed invention can be applied in healthcare, sexology, and sexual pathology, particularly in the devices providing enhancement of sexual sensations during intercourse.

While this invention has been particularly shown and described with references to preferred embodiments thereof, it will be understood by those skilled in the art that various changes in form and details may be made therein without departing from the scope of the invention encompassed by the appended claims.

What is claimed is:

1. An anatomical device for a penis comprising:
   unclosed curvilinear frame with distal ends, forming an aperture for receiving the penis;
   the unclosed curvilinear frame being made of a material with shape memory effect and forming a compressing element which is set to memorize the shape of the curvilinear figure repeating an external contour of the penis's base in erected state;
   wherein a shape setting area of the frame is 30-50% less than that of a cross-section of the penis's base at maximum erection.

2. The anatomical device as described in claim 1, wherein the compressing element is made of the shape memory material that allows for 5 to 10 times increase in the compressing element rigidity while in the active working state, as compared to its initial condition.

3. The anatomical device as in claim 1, wherein the unclosed curvilinear frame is covered by an easily deformable or flexible material.

4. The anatomical device as in claim 1, wherein the distal ends are connected with an easily deformable or flexible material, thus forming a closed curvilinear frame.

5. The anatomical device as described in claim 1, wherein the unclosed curvilinear frame is covered by an easily deformable or flexible material, thus forming a closed curvilinear frame.

6. The anatomical device as described in claim 4, wherein the closed curvilinear frame forms a loop of the easily deformable or flexible material behind the distal ends for releasing a urethra in the penis.

7. The anatomical device as described in claim 5, wherein the closed curvilinear frame forms a loop of the easily deformable or flexible material behind the distal ends for releasing a urethra in the penis.

8. The anatomical device as described in claim 3, wherein the easily deformable or flexible material is made of silicone, elastomer, latex, leather or metal.

9. An anatomical device for a penis comprising:
   a closed curvilinear frame comprising an unclosed curvilinear frame with connected distal ends forming an aperture for receiving the penis;
   the unclosed curvilinear frame being made of a material with shape memory effect, forming a compressing element that is set to memorize the shape of a curvilinear figure repeating an external contour of the penis's base in erected state;
   wherein the area of the setting shape of the frame is 30-50% less than that of the cross-section of the penis's base at maximum erection, and
   wherein in active working state the closed curvilinear frame forms a loop behind the distal ends for releasing a urethra.

10. The anatomical device as described in claim 9, wherein the compressing element is made of the shape memory material that allows for 5 to 10 times increase in the compressing element rigidity while in the active working state, as compared to its initial condition.

11. The anatomical device as described in claim 9, wherein the distal ends are connected by an easily deformable or flexible material, forming the closed curvilinear frame.

12. The anatomical device as described in claim 9, wherein the unclosed curvilinear frame is covered by an easily deformable or flexible material, thus forming a closed curvilinear frame.

13. The anatomical device as described in claim 11, wherein the easily deformable or flexible material is made of silicone, elastomer, latex, leather, or metal.

14. The anatomical device as described in claim 12, wherein the easily deformable or flexible material is made of silicone, elastomer, latex, leather, or metal.

15. An anatomical device comprising:
   a closed curvilinear frame comprising an unclosed curvilinear frame with connected distal ends forming two parts with different rigidities and an aperture for receiving a penis;
   the greater part of the closed curvilinear frame being made of a material with shape memory effect forming a compressing element of greater rigidity compared to the other part, the other part being made of an easily deformable or flexible material, which in its working state forms a loop behind the distal ends for releasing a urethra,
   wherein the compressing element is set to memorize the shape of the curvilinear figure repeating the external contour of a penis base in erected state, the area of the setting shape being 30 to 50% less than that of a cross-section of the penis base at maximum erection.

16. The anatomical device as described in claim 15, wherein the compressing element is made of the shape memory material that allows for 5 to 10 times increase in the compressing element rigidity while in the active working state, as compared to its initial condition.

17. The anatomical device as described in claim 15, wherein the easily deformable or flexible material is made of silicone, elastomer, latex, leather, or metal.

18. The anatomical device as described in claim 16, wherein the easily deformable or flexible material is made of silicone, elastomer, latex, leather, or metal.

* * * * *